(12) United States Patent
Keirsgieter

(10) Patent No.: US 7,726,699 B2
(45) Date of Patent: Jun. 1, 2010

(54) DENTAL TREATMENT APPARATUS

(75) Inventor: Petrus Jacobus Keirsgieter, Fien de la Marstraat 27, NL-1902 MT Castricum (NL)

(73) Assignees: Okey Holding BV, Mt Castricum (NL); Petrus Jacobus Keirsgieter, Mt Castricum (NL)

( * ) Notice: Subject to any disclaimer, the term of this patent is extended or adjusted under 35 U.S.C. 154(b) by 337 days.

(21) Appl. No.: 10/597,670

(22) PCT Filed: Feb. 1, 2005

(86) PCT No.: PCT/NL2005/000070
§ 371 (c)(1),
(2), (4) Date: Apr. 9, 2007

(87) PCT Pub. No.: WO2005/079698
PCT Pub. Date: Sep. 1, 2005

(65) Prior Publication Data
US 2008/0063996 A1    Mar. 13, 2008

(30) Foreign Application Priority Data
Feb. 4, 2007    (NL) ................................ 1025397

(51) Int. Cl.
*F16L 37/00*    (2006.01)
*F16L 39/00*    (2006.01)
*A61C 1/08*    (2006.01)

(52) U.S. Cl. .................. 285/305; 285/124.1; 433/126
(58) Field of Classification Search .............. 433/27, 433/77, 78, 79, 82, 84, 98, 99, 100, 126, 433/146; 285/82, 305, 318, 124.1–124.5, 285/315, 316
See application file for complete search history.

(56) References Cited

U.S. PATENT DOCUMENTS

| | | | | | |
|---|---|---|---|---|---|
| 2,260,373 | A | * | 10/1941 | Gibbs | 407/97 |
| 2,935,338 | A | * | 5/1960 | Mills, Jr. | 251/149.5 |
| 3,082,394 | A | * | 3/1963 | Hahn et al. | 439/191 |
| 4,026,581 | A | * | 5/1977 | Pasbrig | 285/24 |
| 4,139,222 | A | * | 2/1979 | Loland | 285/27 |
| 4,403,959 | A | * | 9/1983 | Hatakeyama | 433/126 |
| 5,039,304 | A | * | 8/1991 | Heil | 433/126 |
| 5,316,347 | A | * | 5/1994 | Arosio | 285/26 |
| 5,476,379 | A | * | 12/1995 | Disel | 433/29 |
| 5,806,832 | A | * | 9/1998 | Larbuisson | 251/149.6 |
| 6,783,379 | B2 | * | 8/2004 | Kerscher et al. | 439/191 |

* cited by examiner

*Primary Examiner*—Cris L Rodriguez
*Assistant Examiner*—Michael R Ballinger
(74) *Attorney, Agent, or Firm*—Egbert Law Offices PLLC

(57) ABSTRACT

Apparatus for dental treatment includes a base, a treatment unit, and a connecting piece. The treatment unit has one or more treatment instruments and one or more lines for the supply of water, air and electricity. The connecting piece is placed in between the base and the treatment unit. The treatment unit can be disconnected from and connected to the base by using the connecting piece.

10 Claims, 2 Drawing Sheets

DENTAL TREATMENT APPARATUS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The invention relates to an dental treatment apparatus. More particularly, the present invention relates to dental treatment apparatus having a base and a treatment unit in which the treatment unit includes several treatment instruments and several lines for the supply of water, air and electricity.

2. Description of Related Art Including Information Disclosed Under 37 CFR 1.97 and 37 CFR 1.98

Dental treatment apparatus having a base and a treatment unit in which the treatment unit has several treatment instruments and several lines for the supply of water, air and electricity is known in the art. However, the dental treatment apparatus of the prior art has a particular drawback. In particular, when the dental treatment apparatus must be serviced or when, as a result of a malfunction, repairs must be made, the entire apparatus is out of use until the repair or servicing activities are completed.

It is an object of the present invention to overcome this drawback of the prior art dental treatment apparatus.

BRIEF SUMMARY OF THE INVENTION

The present invention utilizes a connecting apparatus between the base and the treatment unit. This connecting apparatus allows the treatment unit to be disconnected from and connected to the base. Through the use of the apparatus of the present invention, it is possible to incorporate the components of the dental treatment apparatus and to disconnect the treatment apparatus from the base. The connecting apparatus allows these parts to be interchangeable so as to facilitate service and repair.

The connecting apparatus of the present invention is formed by first part and a second part that are provided with cooperating connector ports for the supply of water, air and electricity. When the first part and the second part are coupled to each other, the connector ports are connected to each other in such a way that the water lines, air lines and electricity lines from the base to the treatment unit are established. The second part is provided with an opening through which a translatable pin is movable. The translatable pin has an outer end that is fixed to a cable. The translatable pin has an inner flanged member and an outer flanged member at the opposite end from the cable. The inner flanged member is spaced from the outer flanged member in generally parallel relationship. A spring extends between the inner flanged member and a surface of the second part. In this manner, the translatable pin is supported on the second part and allows the translatable pin to be drawn against spring force through the opening in the second part by the cable.

The first part is provided with a first opening having a diameter that is greater than the diameter of the outer flanged member. A key slot opens to this first opening. The key slot has a diameter that is smaller than the diameter of the outer flanged member but is larger than the diameter of the translatable pin. As such, when the first part is placed into a proper position, the key slot is placed between the outer flanged member and the inner flanged member and leans against the outer flanged member. When the cable is pulled, the first part is moved towards the second part in such a way that the connector ports are coupled together.

The second part is provided with a sleeve in which the translatable pin is movable. The spring is supported on the second part by this sleeve.

One of the first and seconds is provided with at least two guide pins and the other of the first and second part is provided with at least two guide holes for receiving the guide pins. In this manner, the first part can be connected to the second part in a fixed orientation.

DETAILED DESCRIPTION OF THE INVENTION

Figure 1:
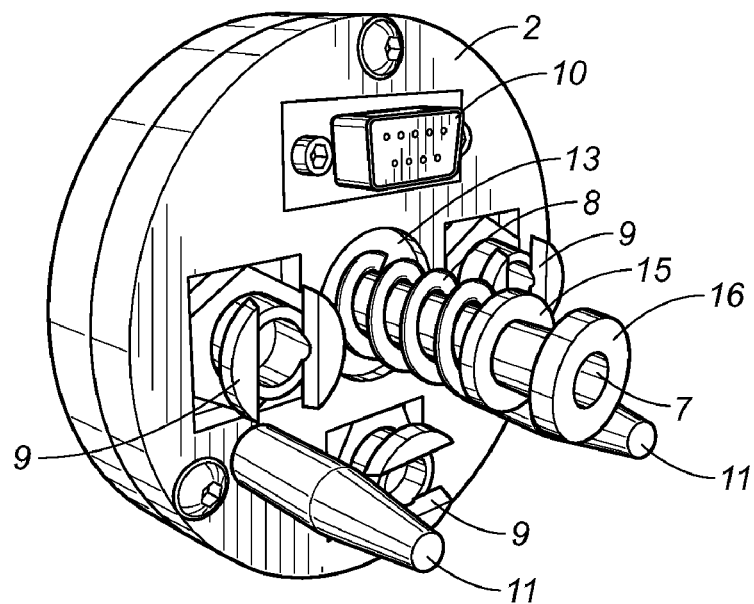
FIG. 1 is a perspective view showing the second part.
Figure 2:
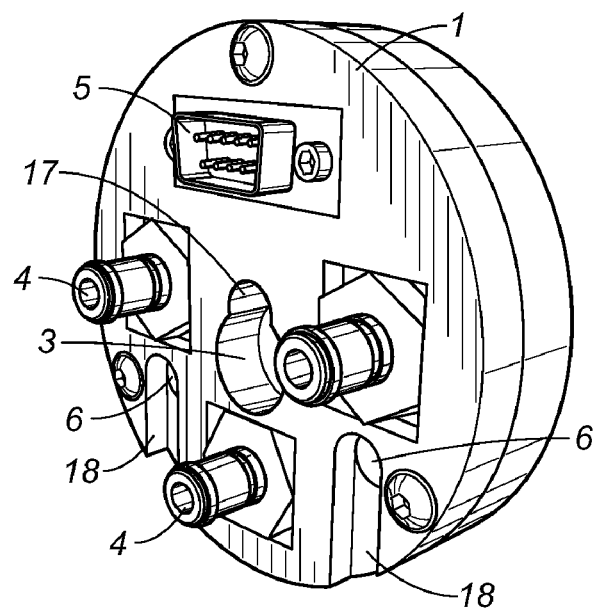
FIG. 2 is a perspective view of the first part.
Figure 3A:
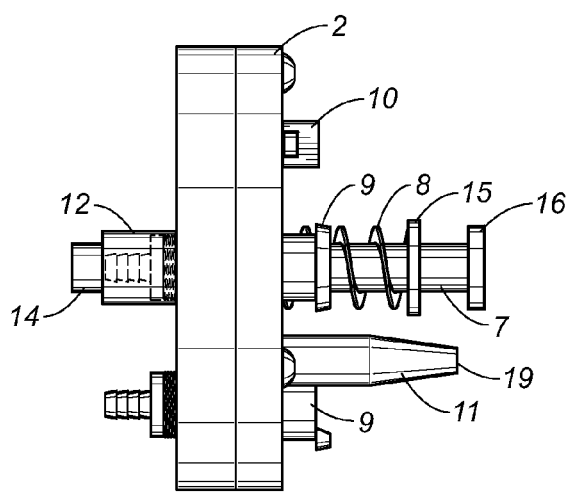
FIG. 3a shows a side view of the second part.
Figure 3B:
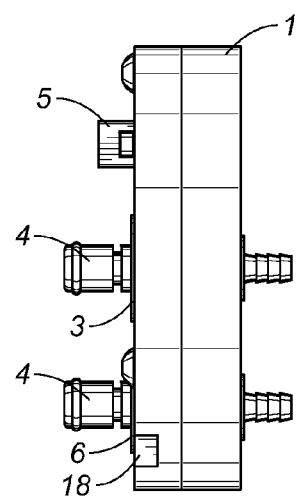
FIG. 3b shows a side view of the first part.

As can be seen in the FIGS. 1 through 3b, the connecting apparatus of the present invention is formed by a first part 1 and a second part 2 having connector ports 4 and 9 for the supply of water and air. The first part 1 and the second part 2 are further provided with connector ports 5 and 10 for the supply of electricity. When the first part 1 and the second part 2 are coupled to each other, the connector ports 4 and 9 and the connector ports 5 and 10 are connected to each other. In the preferred embodiment of the present invention, the first part 1 is provided with three male connector ports 4 for the supply of water and air. The second part 2 is provided with three female connector ports 9 for the supply of water and air. When the connector ports 4 are connected to the connector ports 9 and when the connector port 5 is connected to the connector port 10, the lead-through of water, air and electricity from the base to the treatment unit is established. When disconnecting the connections between the connector ports 4 and 9, the couplings for the water and air supply are automatically closed. As a result, no "leak water" and "leak air" develops. As can be seen in the figures, the electronics are passed through the upper connector ports 5 and 10. As a result of this, any "post dripping" after the disconnection of the water connector ports will cause no short-circuiting to occur.

The second part 2 is provided with a central opening 13 through which a translatable pin 7 is movable. The translatable pin 7 at one outer end 14 is fixed to a cable 20. The opposite end is provided with an inner flanged member 15 and an outer flanged member 16. The inner flanged member 15 is in spaced parallel relationship to the outer flanged member 16. A spring is positioned between the inner flanged member 15 and surface of the second part 2. As a result, translatable pin 7 is supported on the second part 2. In this manner, the translatable pin 7 can be drawn against spring force through the opening 13 by the cable 20.

The first part 1 is provided with a central first opening 3 having a diameter such that this can be moved over the outer flanged member 16. The first opening 3 extends into a key slot 17. The key slot 17 has a diameter which is smaller than the diameter of the outer flanged member 16 but is larger that the diameter of the translatable pin 7. When the first part 1 with the key slot 17 is placed in between the inner flanged member 15 and the outer flanged member 16 and leans against the outer flanged member 16, the pulling of the cable causes the first part 1 to be moved toward the second part 2. In this manner, the connector ports 4 and 9 and the connector ports 5 and 10 are coupled to each other.

In the illustrated embodiment of the present invention, the second part 2 is provided with a guide sleeve 12 in which the translatable pin 7 is movable. The spring 8 is supported on the second part 2 by means of the sleeve 12.

The second part 2 is provided with at least two conical-shaped guide pins 11. The first part 1 is provided with at least two guide holes 6 for receiving the guide pins 11. The guide pins 11 have a length such that the outer ends 19 thereof extend beyond the inner flanged member 15 of the translatable pin 7 when the translatable pin 7 is pushed out by the spring 8. Additionally, the guide slots 18 extend into the guide holes 6 for receiving the outer ends 19 of the guide pins 11. In this manner, when the parts 1 and 2 are connected to each other and when the translatable pin 7 is moved from the first opening 3 into the key slot 17, the outer ends 19 of the guide pins 11 are forced by means of the guide slots 18 into the guide holes 6.

Through the construction of the present invention, the female and male connectors for the supply of water, air and electricity will gradually couple with each other. The first part and the second part can be connected to each other in a fixed position. The space between the inner flanged member 15 and the outer flanged member 16 of the translatable pin 7 is only somewhat larger than the thickness of the first part 1. As such, the first part 1 will fit closely therebetween. In this manner, the displacement or tilting of the second part 2 relative to the first part 1 is prevented. The diameter of the inner flanged member 15 is larger than the diameter of the first opening 3 so as to prevented the first part to be pushed over the inner flanged member 15 during the coupling of the first part 1 to the second part 2.

By virtue of the present invention, it is possible to incorporate the technical portions of the dental treatment apparatus in a treatment unit and to disconnect this treatment unit from the base. As such, it is possible to mount all of the technical parts, in particular those parts that are susceptible to malfunction, as part of an interchangeable unit. When the cable releases the translatable pin 7, the first part 1 will be pushed away from the second part 2 by the force of the pressure spring 8 and by the springs in the water and air connectors 4 and 9. The water and air connections automatically are closed after the opening of the coupling.

Through the use of these three types of connectors, it is possible to mount all the electronics in the treatment unit. Because of this, it is very simple to interchange the treatment unit in the case of a malfunction or breakdown.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A connecting apparatus for use between a base and a treatment unit of a dental instrument assembly, the treatment unit having lines for supplying water, air or electricity, the connecting apparatus comprising: a translatable portion a first part having connector ports suitable for connection to the lines of the treatment unit; and a second part having connector ports thereof, said second part being suitable for coupling to said first part, said second part having an opening through which said translatable pin is movable, said translatable pin having a first end fixed to a cable, said translatable pin having an outer flanged member and an inner flanged member at a second end thereof, said outer flanged member being in spaced parallel relation to said inner flanged member, said second part having a surface facing said first part, said translatable pin having a spring interposed between said inner flanged member and said surface of said second part so as to support said translatable pin in position relative to said second part, said cable suitable for moving said translatable pin through said opening against a force of said spring, said first part having a first opening of a diameter greater than a diameter of said outer flanged member, said first part having a key slot radially opening to said first opening, said key slot having a diameter that is less than said diameter of said outer flanged member and larger than a diameter of said translatable pin, said key slot suitable for receiving said translatable pin therein an area between said outer flanged member and said inner flanged member so as to lean against said outer flanged member, said cable suitable for pulling on said translatable pin so as to draw said first part toward said second part such that said connector ports of said first part are coupled to said connector ports of said second part.

2. The connecting apparatus of claim 1, wherein said second part has a sleeve, said translatable pin extending through said sleeve, said sleeve supporting said spring on said second part.

3. The connecting apparatus of claim 1, wherein one of said first and second parts has at least a pair of guide pins, the other of said first and second parts having at least a pair of guide holes receiving the guide pins therein so as to fix a position of said first part relative to said second part.

4. The connecting apparatus of claim 3, wherein the guide pins have a conical shape.

5. The connecting apparatus of claim 3, wherein each of the guide holes have a guide slot suitable for receiving the end of the guide pin so as to allow the guide pin to slide toward the guide hole.

6. The connecting apparatus of claim 1, wherein one of the connector ports of said second part is for an electrical supply, said one of said connector ports being positioned above said translatable pin.

7. The connecting apparatus of claim 1, wherein one of the connector ports of said second part is for an electrical current supply, another of the connector ports of said second part being for a water supply.

8. The connecting apparatus of claim 1, wherein said opening of said second part is located centrally of said second part, said first opening of said first part located centrally of said first part.

9. The connecting apparatus of claim 1, wherein said first part has a thickness, said outer flanged member being spaced from said inner flanged member by a distance slightly greater than the thickness of said first part.

10. The connecting apparatus of claim 1, wherein said first opening has a diameter that is less than a diameter of said inner flanged member.

\* \* \* \* \*